United States Patent
Lunden et al.

(10) Patent No.: US 7,273,703 B2
(45) Date of Patent: Sep. 25, 2007

(54) DETECTION OF MUTATIONS

(75) Inventors: Anne Lunden, Uppsala (SE); Leif Andersson, Uppsala (SE); Stefan Marklund, Uppsala (SE)

(73) Assignee: FunboGen AB, Uppsala (SE)

( * ) Notice: Subject to any disclaimer, the term of this patent is extended or adjusted under 35 U.S.C. 154(b) by 0 days.

(21) Appl. No.: 10/501,032

(22) PCT Filed: Jan. 9, 2003

(86) PCT No.: PCT/IB03/00028

§ 371 (c)(1),
(2), (4) Date: Jan. 6, 2006

(87) PCT Pub. No.: WO03/057886

PCT Pub. Date: Jul. 17, 2003

(65) Prior Publication Data

US 2006/0147910 A1    Jul. 6, 2006

(30) Foreign Application Priority Data

Jan. 9, 2002    (DK) ............................... 2002 00031

(51) Int. Cl.
*C12Q 1/68*  (2006.01)
*C07H 21/04*  (2006.01)
*C12N 9/06*  (2006.01)
*C12P 21/06*  (2006.01)

(52) U.S. Cl. ................... 435/6; 435/191; 435/69.1; 435/320.1; 435/325; 536/23.2

(58) Field of Classification Search ............... 435/6, 435/191, 69.1; 536/23.2
See application file for complete search history.

(56) References Cited

FOREIGN PATENT DOCUMENTS

| WO | WO98/23603 | | 6/1998 |
|---|---|---|---|
| WO | WO 01/23603 | * | 9/2000 |
| WO | WO 01/23603 | * | 4/2001 |

OTHER PUBLICATIONS

Akerman et al., "Two Novel Mutations of the *FMO3* Gene in a Proband with Trimethylaminuria," *Human Mutation,* 1999, 13:376-379.
Al-Waiz et al., "A genetic polymorphism of the *N*-oxidation of trimethylamine in humans," *Clin. Pharmacol. Ther.,* 1987, 42:588-594.
Al-Waiz et al., "Trimethylaminuria: The Detection of Carriers Using a Trimethylamine Load Test," *J. Inher. Metab. Dis.,* 1989, 12:80-85.
Al-Waiz et al., "Trimethylaminuria (Fish-Odour Syndrome): An Inborn Error of Oxidative Metabolism," *The Lancet,* 1987, p. 634.
Al-Waiz et al., "The metabolism of $^{14}$C-labelled trimethylamine and its *N*-oxide in man," *Xenobiotica,* 1987, 17(5):551-558.
Ayesh et al., "The fish odour syndrome: biochemical, familial, and clinical aspects," *BMJ,* 1993, 307:655-657.

Ayesh and Smith, "Genetic Polymorphism of Trimethylamine N-Oxidation," *Pharmac. Ther.,* 1990, 45:387-401.
Basarab et al., "Sequence variations in the flavin-containing monooxygenase 3 gene (FMO3) in fish odour syndrome," *Br. J. Dermatol.,* 1999, 140:164-167.
Bolton et al., "The Hen's Egg: Genetics of Taints in Eggs from Hens Fed on Rapeseed Meal," *Br. Poult Sci.,* 1976, 17:313-320.
Burnett et al., "Cloning and Sequencing of Flavin-containing Monooxygenases FMO3 and FMO4 from Rabbit and Characterization of FMO3," *J. Biol. Chem.,* 1994, 269(19):14314-14322.
Corfield, "Bacterial Fishiness in Milk" *Dairy Industries,* 1955, pp. 1035-1037.
Culbertson, "RNA surveillance unforeseen consequences for gene expression, inherited genetic disorders and cancer," *TIG,* 1999, 15(2):74-80.
Dolphin et al., "Missense mutation in flavin-containing monooxygenase 3 gene, *FMO3*, underlies fish-odour syndrome," *Nature Genetics,* 1997, 17:491-494.
Dolphin et al., "Structural Organization of the Human Flavin-Containing Monooxygenase 3 Gene (*FMO3*), the Favored Candidate for Fish-Odor Syndrome, Determined Directly from Genomic DNA," *Genomics,* 1997, 46:260-267.
Eyer et al., "Investigation of the "fishy" odour in coffee creamer," *Milchw. Forschung,* 1990, 19:43-45.
Forrest et al., "A novel deletion in the flavin-containing Monooxygenase gene (*FMO3*) in a Greek patient with trimethylaminuria," *Pharmacogenetics,* 2001, 11:169-174.
Hlavica and Kehl, "Studies on the Mechanism of Hepatic Microsomal *N*-Oxide Formation. The Role of Cytochrome *P*-450 and Mixed-Function Amine Oxidase in the *N*-Oxidation of *NN*-Dimethylaniline," *Biochem. J.,* 1977, 164:487-496.
Hobson-Frohock et al., "Egg Taints: Association with Trimethylamine," *Nature,* 1973, 243:304-305.
Humbert et al., "Trimethylaminuria: The Fish-Odour Syndrome," *The Lancet,* 1970, pp. 770-771.
Humphriss, "Chromogenic Bacteria and Milk," *Dairy Industries,* 1953, pp. 781-7782.
Kim et al., "Chemical Test for Detecting Wheat Pasture Flavor in Cow's Milk," *J. Dairy Sci.,* 1980, 63:368-374.
Lundén et al., "A Nonsense Mutation in the *FMO3* Gene Underlies Fishy Off-Flavor in Cow's Milk," *Genome Research,* 2002, 12:1885-1888.

(Continued)

*Primary Examiner*—Rebecca E. Prouty
*Assistant Examiner*—M. Younus Meah
(74) *Attorney, Agent, or Firm*—Fish & Richardson P.C.

(57) ABSTRACT

The present invention relates to a polypeptide which is a flavin-containing monooxygenase 3 (FMO3), wherein said FMO3 is a polypeptide comprising at least a sequence having at least 85% identity with the polypeptide sequence SEQ ID NO: 15, in particular to a polypeptide which is a functionally altered mutant of flavin-containing mono oxygenase 3 (FMO3) leading to a buildup of trimethylamine in an animal. Further, the invention relates to nucleic acid sequences encoding said polypeptide, and to the complements of such nucleic acid sequences. Such nucleic acid sequences and fragments thereof may be useful e.g. as primers. The invention further relates to various methods for determining the presence in e.g. a nucleic acid sample of a nucleic acid sequence encoding a mutated FMO3 polypeptide.

7 Claims, 1 Drawing Sheet

OTHER PUBLICATIONS

Mehta et al., "Trimethylamine Responsible for Fishy Flavor in Milk from Cows on Wheat Pasture," *J. Dairy Sci.*, 1973, 57(3):285-289.

Pearson et al., "The Effect of Thionamides and Related Compounds on Trimethylamine Oxidase Activity in Hepatic Microsomes Isolated From Chickens (*Gallus Domesticus*)," *Comp. Biochem. Physiol.*, 1982, 73C:389-393.

Pearson et al., "Effect of Rapeseed Meal on Trimethylamine Metabolism in the Domestic Fowl in Relation to Egg Taint," *J. Sci. Food Agric.*, 1979, 30:799-804.

Phillips et al., "The molecular biology of the flavin-containing monooxygenases of man," *Chemico-Biological Interactions*, 1995, 96:17-32.

Ronaghi et al., "A Sequencing Method Based on Real-Time Pyrophosphate," *Science*, 1998, 281:363-364.

Spellacy and Watts, "Trimethylaminuria," *J. Inher. Metab. Dis.*, 1979, 2:85-88.

Swoboda and Peers, "Volatile Odorous Compounds Responsible for Metallic, Fishy Taint Formed in Butterfat by Selective Oxidation," *J. Sci. Fd. Agric.*, 1977, 28:1010-1018.

Treacy et al., "Mutations of the flavin-containing monooxygenase gene (*FMO3*) cause trimethylaminuria, a defect in detoxication," *Human Molecular Genetics*, 1998, 7(5):839-845.

Von Gunten et al., "Factors Related to the Occurrence of Trimethylamine in Milk," *J. Milk Food Technol.*, 1976, 39(8):526-529.

Zhang et al., "Dietary Precursors of Trimethylamine in Man: A Pilot Study," *Food and Chemical Toxicology*, 1999, 37:515-520.

GenBank Accession No. AF488422 dated Sep. 27, 2002.

GenBank Accession No. AF488417 dated Sep. 27, 2002.

\* cited by examiner

SEQUENCE LISTING

```
<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
gaccatgcag aagagggcag                                              20
```

<210> SEQ ID NO 2
<211> LENGTH: 27
<212> TYPE: DNA
<213> ORGANISM: Artificial Sequence
<220> FEATURE:
<223> OTHER INFORMATION: Primer

<400> SEQUENCE: 2
cttaaactgt atgtatttca ggaggtt                               27

<210> SEQ ID NO 3
<211> LENGTH: 21
<212> TYPE: DNA
<213> ORGANISM: Artificial Sequence
<220> FEATURE:
<223> OTHER INFORMATION: Primer

<400> SEQUENCE: 3
catcatcagc tccagaagtg g                                     21

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
taaaggcatc aagccatagt t                                     21

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
cagaatcctg aggaaagagc c                                     21

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
attacttgtg ctgcccagcg                                       20

<210> SEQ ID NO 7
<211> LENGTH: 26
<212> TYPE: DNA
<213> ORGANISM: Artificial Sequence
<220> FEATURE:
<223> OTHER INFORMATION: Primer

<400> SEQUENCE: 7
gatgaatgat attaatgaga aaatgg                                26

<210> SEQ ID NO 8
<211> LENGTH: 18
<212> TYPE: DNA
<213> ORGANISM: Artificial Sequence
<220> FEATURE:
<223> OTHER INFORMATION: Primer

```
<400> SEQUENCE: 8
ccggtcccac tgggtcag                                                    18

<210> SEQ ID NO 9
<211> LENGTH: 142
<212> TYPE: DNA
<213> ORGANISM: Bos taurus
<220> FEATURE:
<221> NAME/KEY: exon
<222> LOCATION: (2)..(142)
<223> OTHER INFORMATION:

<400> SEQUENCE: 9 g gcc agc att tat cgg tca gtc ttt acc aac tct tcc aaa gag atg aca    49
  Ala Ser Ile Tyr Arg Ser Val Phe Thr Asn Ser Ser Lys Glu Met Thr
    1               5                  10                  15 tgt ttt cca gac ttt cca ttt cct gat gat ttt cct aac ttt atg cac      97
Cys Phe Pro Asp Phe Pro Phe Pro Asp Asp Phe Pro Asn Phe Met His
                 20                  25                  30 aac agc aag ctc cag gaa tat att act atg ttt gcc aaa gaa aag         142
Asn Ser Lys Leu Gln Glu Tyr Ile Thr Met Phe Ala Lys Glu Lys
         35                  40                  45

<210> SEQ ID NO 10
<211> LENGTH: 151
<212> TYPE: DNA
<213> ORGANISM: Bos taurus
<220> FEATURE:
<221> NAME/KEY: exon
<222> LOCATION: (2)..(151)
<223> OTHER INFORMATION:

<400> SEQUENCE: 10 c tcc tgg gtg atg agc cgg gtc tgg gat gaa ggc tat cca tgg gac atg    49
  Ser Trp Val Met Ser Arg Val Trp Asp Glu Gly Tyr Pro Trp Asp Met
    1               5                  10                  15 ctg ttt atc act cga ttt gaa aca ttc ctc aag aac acc tta ccg aca      97
Leu Phe Ile Thr Arg Phe Glu Thr Phe Leu Lys Asn Thr Leu Pro Thr
                 20                  25                  30 gtc att tct aac tgg tgg tac atg aag caa atg aac gcc aga ttc aag     145
Val Ile Ser Asn Trp Trp Tyr Met Lys Gln Met Asn Ala Arg Phe Lys
         35                  40                  45 cac gag                                                             151
His Glu
     50

<210> SEQ ID NO 11
<211> LENGTH: 313
<212> TYPE: DNA
<213> ORGANISM: Bos taurus
<220> FEATURE:
<221> NAME/KEY: exon
<222> LOCATION: (2)..(313)
<223> OTHER INFORMATION:

<400> SEQUENCE: 11 t gtg ttc aat gac gaa ctc cca gct tgc att tta tgt ggc att gtg acc    49
  Val Phe Asn Asp Glu Leu Pro Ala Cys Ile Leu Cys Gly Ile Val Thr
    1               5                  10                  15 att aag cca aat gtg aag gag ttt aca gag gat tca gct att ttt gag      97
Ile Lys Pro Asn Val Lys Glu Phe Thr Glu Asp Ser Ala Ile Phe Glu
                 20                  25                  30 gat ggg acg gtg ttt aag gcc att gac tat gtc atc ttt gca aca ggc     145
Asp Gly Thr Val Phe Lys Ala Ile Asp Tyr Val Ile Phe Ala Thr Gly
         35                  40                  45
```

| | | | | | | | | | | | | | | | |
|---|---|---|---|---|---|---|---|---|---|---|---|---|---|---|---|
| tat | agt | tat | gcc | tac | ccc | ttc | ctt | gat | gac | tcc | atc | att | aag | agc | aga | 193 |
| Tyr | Ser | Tyr | Ala | Tyr | Pro | Phe | Leu | Asp | Asp | Ser | Ile | Ile | Lys | Ser | Arg |
| | 50 | | | | 55 | | | | | 60 | | | | | |

| gac | aat | gag | gtc | acc | tta | ttt | aaa | ggc | ata | ttc | cca | cct | cca | ctg | gaa | 241 |
| Asp | Asn | Glu | Val | Thr | Leu | Phe | Lys | Gly | Ile | Phe | Pro | Pro | Pro | Leu | Glu |
| 65 | | | | 70 | | | | | 75 | | | | | 80 | |

| aag | cca | acc | ttg | gct | gtg | atc | ggc | ctt | gtc | cag | tcc | ctt | gga | gct | gcc | 289 |
| Lys | Pro | Thr | Leu | Ala | Val | Ile | Gly | Leu | Val | Gln | Ser | Leu | Gly | Ala | Ala |
| | | | | 85 | | | | | 90 | | | | | 95 | |

| atc | ccc | act | act | gac | ctg | cag | tct | | | | | | | | | 313 |
| Ile | Pro | Thr | Thr | Asp | Leu | Gln | Ser |
| | | | 100 | | | | |

<210> SEQ ID NO 12
<211> LENGTH: 202
<212> TYPE: DNA
<213> ORGANISM: Bos taurus
<220> FEATURE:
<221> NAME/KEY: exon
<222> LOCATION: (2)..(202)
<223> OTHER INFORMATION:

<400> SEQUENCE: 12

| g | ttt | ggc | aaa | agt | gat | acc | ata | cag | acg | gat | tat | gtt | gtt | tat | atg | gat | 49 |
|---|---|---|---|---|---|---|---|---|---|---|---|---|---|---|---|---|---|
| | Phe | Gly | Lys | Ser | Asp | Thr | Ile | Gln | Thr | Asp | Tyr | Val | Val | Tyr | Met | Asp |
| | 1 | | | | 5 | | | | | 10 | | | | | 15 | |

| gag | ctt | gcc | tcc | ttc | att | ggg | gca | aag | ccc | aac | atc | cca | tgg | ctg | ttt | 97 |
| Glu | Leu | Ala | Ser | Phe | Ile | Gly | Ala | Lys | Pro | Asn | Ile | Pro | Trp | Leu | Phe |
| | | | 20 | | | | | 25 | | | | | 30 | | |

| ctc | aca | gat | cca | aag | ttg | gca | ttg | gag | gtc | tac | ttt | ggc | cct | tgc | acc | 145 |
| Leu | Thr | Asp | Pro | Lys | Leu | Ala | Leu | Glu | Val | Tyr | Phe | Gly | Pro | Cys | Thr |
| | | 35 | | | | | 40 | | | | | 45 | | | |

| cca | tac | cag | ttt | agg | ctg | gtg | ggc | cca | gga | aag | tgg | cca | gga | gcc | aga | 193 |
| Pro | Tyr | Gln | Phe | Arg | Leu | Val | Gly | Pro | Gly | Lys | Trp | Pro | Gly | Ala | Arg |
| | 50 | | | | 55 | | | | | 60 | | | | | |

| aac | gcc | atc | | | | | | | | | | | | | | 202 |
| Asn | Ala | Ile |
| 65 | | |

<210> SEQ ID NO 13
<211> LENGTH: 714
<212> TYPE: DNA
<213> ORGANISM: Bos taurus
<220> FEATURE:
<221> NAME/KEY: Intron
<222> LOCATION: (1)..(714)
<223> OTHER INFORMATION:
<220> FEATURE:
<221> NAME/KEY: Intron
<222> LOCATION: (1)..(714)
<223> OTHER INFORMATION:

<400> SEQUENCE: 13
ctcagattgt aagagcatct gtggtaaagg ggatccagaa ttttcatagc aaaatttgac    60
tttgtaaata cttaaactgt tttagtcttg aatactcctg agtgggacca ttagggtgac   120
agctatgagc taaattcagc cattcaacaa atagttatca aggatatact tcgcacctga   180
tagaccacta aatcctgttt cagccctcca tatctcctgc aatatatcat aaaagagaga   240
cccagaaaga ttaaatttca gaggagcttg gaacacacg gatgtggact tctatttct    300 agctcataca tcctctaaaa tgtaaggatg ccttccaata ggtggctcta ataaatgact   360
cagccacaca acaactagtc agaagaacta ggctccagtc ctacctctgt cactaatcag   420

| | |
|---|---|
| ctcagtggcc atgaattaat aactacacgt gagcaagaga caattcctct acttgtaaat | 480 |
| gtggataaaa atgcctttct cagcagcctt gttgtgttgt ggaatgtcca agtgagatca | 540 |
| gtatgaaagt ccttcagtaa aatctacaaa gtactggata atgagcaata atccccttac | 600 |
| caacaaaagg atcgatgttg atttgcgtgg ataaaaaggt gtgaggcatt ttccctgttc | 660 |
| ttgtttctaa aggaagctcg gatagccaca gtcttgtttc tctccctcct ctag | 714 |

```
<210> SEQ ID NO 14
<211> LENGTH: 1672
<212> TYPE: DNA
<213> ORGANISM: Bos taurus
<220> FEATURE:
<221> NAME/KEY: CDS
<222> LOCATION: (18)..(1616)
<223> OTHER INFORMATION:
<220> FEATURE:
<221> NAME/KEY: mRNA
<222> LOCATION: (1)..(1672)
<223> OTHER INFORMATION:

<400> SEQUENCE: 14
```

| | |
|---|---|
| attacagaaa ggtaact atg gtg aag aaa gtg gcc atc att gga gca ggc<br>                     Met Val Lys Lys Val Ala Ile Ile Gly Ala Gly<br>                      1            5                     10 | 50 |
| atc agt ggc ctg gcc tcc atc aga aac tgc cta gaa gag gga ctg gaa<br>Ile Ser Gly Leu Ala Ser Ile Arg Asn Cys Leu Glu Glu Gly Leu Glu<br>           15                     20                     25 | 98 |
| ccc acc tgc ttt gag aag ggt gaa gac att ggg ggc ctg tgg aaa ttc<br>Pro Thr Cys Phe Glu Lys Gly Glu Asp Ile Gly Gly Leu Trp Lys Phe<br>      30                     35                    40 | 146 |
| tcg gac cat gta gag gaa ggc agg gcc agc att tat cgg tca gtc ttt<br>Ser Asp His Val Glu Glu Gly Arg Ala Ser Ile Tyr Arg Ser Val Phe<br>    45                     50                     55 | 194 |
| acc aac tct tcc aaa gag atg aca tgt ttt cca gac ttt cca ttt cct<br>Thr Asn Ser Ser Lys Glu Met Thr Cys Phe Pro Asp Phe Pro Phe Pro<br>60                     65                     70                     75 | 242 |
| gat gat ttt cct aac ttt atg cac aac agc aag ctc cag gaa tat att<br>Asp Asp Phe Pro Asn Phe Met His Asn Ser Lys Leu Gln Glu Tyr Ile<br>                 80                     85                     90 | 290 |
| act atg ttt gcc aaa gaa aag aac ctc ctg aaa tac ata caa ttt aag<br>Thr Met Phe Ala Lys Glu Lys Asn Leu Leu Lys Tyr Ile Gln Phe Lys<br>           95                    100                   105 | 338 |
| aca att gta tcc agt gta aat aag cgt ccc gat ttc caa acc act ggc<br>Thr Ile Val Ser Ser Val Asn Lys Arg Pro Asp Phe Gln Thr Thr Gly<br>           110                   115                   120 | 386 |
| caa tgg gat gtt atc act gaa aag gat ggt aaa aag gaa tca gct gtc<br>Gln Trp Asp Val Ile Thr Glu Lys Asp Gly Lys Lys Glu Ser Ala Val<br>    125                     130                   135 | 434 |
| ttt gat gcc gta atg att tgt tct gga cat cat gtg tac ccc aac ata<br>Phe Asp Ala Val Met Ile Cys Ser Gly His His Val Tyr Pro Asn Ile<br>140                    145                     150                   155 | 482 |
| cct aaa gag tcc ttt cca gga ata aaa ctt ttt aaa ggc aaa tgc ttc<br>Pro Lys Glu Ser Phe Pro Gly Ile Lys Leu Phe Lys Gly Lys Cys Phe<br>                    160                   165                   170 | 530 |
| cac agc cgg gac tat aaa gaa cca gga atc ttc aag ggg aag cga gtc<br>His Ser Arg Asp Tyr Lys Glu Pro Gly Ile Phe Lys Gly Lys Arg Val<br>           175                   180                   185 | 578 |
| ctg gtg att ggt ctg ggg aac tca ggc tgt gac atc gcc tca gaa ctc<br>Leu Val Ile Gly Leu Gly Asn Ser Gly Cys Asp Ile Ala Ser Glu Leu<br>    190                     195                   200 | 626 |
| agc cac ata gct gaa aaa gtc atc atc agc tcc cga agt ggc tcc tgg | 674 |

```
            Ser His Ile Ala Glu Lys Val Ile Ile Ser Ser Arg Ser Gly Ser Trp
                205                 210                 215 gtg atg agc cgg gtc tgg gat gaa ggc tat cca tgg gac atg ctg ttt         722
Val Met Ser Arg Val Trp Asp Glu Gly Tyr Pro Trp Asp Met Leu Phe
220                 225                 230                 235 atc act cga ttt gaa aca ttc ctc aag aac acc tta ccg aca gtc att         770
Ile Thr Arg Phe Glu Thr Phe Leu Lys Asn Thr Leu Pro Thr Val Ile
                240                 245                 250 tct aac tgg tgg tac atg aag caa atg aac gcc aga ttc aag cac gag         818
Ser Asn Trp Trp Tyr Met Lys Gln Met Asn Ala Arg Phe Lys His Glu
            255                 260                 265 aac tac ggc ttg atg cct tta aac agc acc ctg agg aaa gag cct gtg         866
Asn Tyr Gly Leu Met Pro Leu Asn Ser Thr Leu Arg Lys Glu Pro Val
        270                 275                 280 ttc aat gac gaa ctc cca gct tgc att tta tgt ggc att gtg acc att         914
Phe Asn Asp Glu Leu Pro Ala Cys Ile Leu Cys Gly Ile Val Thr Ile
    285                 290                 295 aag cca aat gtg aag gag ttt aca gag gat tca gct att ttt gag gat         962
Lys Pro Asn Val Lys Glu Phe Thr Glu Asp Ser Ala Ile Phe Glu Asp
300                 305                 310                 315 ggg acg gtg ttt aag gcc att gac tat gtc atc ttt gca aca ggc tat        1010
Gly Thr Val Phe Lys Ala Ile Asp Tyr Val Ile Phe Ala Thr Gly Tyr
                320                 325                 330 agt tat gcc tac ccc ttc ctt gat gac tcc atc att aag agc aga gac        1058
Ser Tyr Ala Tyr Pro Phe Leu Asp Asp Ser Ile Ile Lys Ser Arg Asp
            335                 340                 345 aat gag gtc acc tta ttt aaa ggc atc ttc cca cct cca ctg gaa aag        1106
Asn Glu Val Thr Leu Phe Lys Gly Ile Phe Pro Pro Pro Leu Glu Lys
        350                 355                 360 cca acc ttg gct gtg atc ggc ctt gtc cag tcc ctt gga gct gcc atc        1154
Pro Thr Leu Ala Val Ile Gly Leu Val Gln Ser Leu Gly Ala Ala Ile
    365                 370                 375 ccc act act gac ctg cag tct cgc tgg gca gta caa gta att aag gga        1202
Pro Thr Thr Asp Leu Gln Ser Arg Trp Ala Val Gln Val Ile Lys Gly
380                 385                 390                 395 aca tgc cct ttg cct tct gtc aag gac atg atg aat gat att gat gaa        1250
Thr Cys Pro Leu Pro Ser Val Lys Asp Met Met Asn Asp Ile Asp Glu
                400                 405                 410 aaa atg ggg aaa aag ctc aaa ttg ttt ggc aaa agt gat acc ata cag        1298
Lys Met Gly Lys Lys Leu Lys Leu Phe Gly Lys Ser Asp Thr Ile Gln
            415                 420                 425 acg gat tat gtt gtt tat atg gat gag ctt gcc tcc ttc att ggg gca        1346
Thr Asp Tyr Val Val Tyr Met Asp Glu Leu Ala Ser Phe Ile Gly Ala
        430                 435                 440 aag ccc aac atc cca tgg ctg ttt ctc aca gat cca aag ttg gca ttg        1394
Lys Pro Asn Ile Pro Trp Leu Phe Leu Thr Asp Pro Lys Leu Ala Leu
    445                 450                 455 gag gtc tac ttt ggc cct tgc acc cca tac cag ttt agg ctg gtg ggc        1442
Glu Val Tyr Phe Gly Pro Cys Thr Pro Tyr Gln Phe Arg Leu Val Gly
460                 465                 470                 475 cca gga aag tgg cca gga gcc aga aac gcc atc ctg acc cag tgg gac        1490
Pro Gly Lys Trp Pro Gly Ala Arg Asn Ala Ile Leu Thr Gln Trp Asp
                480                 485                 490 cgg tta ctg aaa cct atg acg aca aga gtg gtt ggg agt cct ctg aag        1538
Arg Leu Leu Lys Pro Met Thr Thr Arg Val Val Gly Ser Pro Leu Lys
            495                 500                 505 cct tgc tta ttt tgc aac tgg ttc aga cct gtt ctt att tct gtt gta        1586
Pro Cys Leu Phe Cys Asn Trp Phe Arg Pro Val Leu Ile Ser Val Val
        510                 515                 520
```

```
tca att gct gct ctc att gtg ttg ttc tag ccatcattct atctaggatt       1636
Ser Ile Ala Ala Leu Ile Val Leu Phe
    525                 530 ctgaacatta ctaacaatac ctggaaagaa gcttca                              1672
```

<210> SEQ ID NO 15
<211> LENGTH: 532
<212> TYPE: PRT
<213> ORGANISM: Bos taurus

<400> SEQUENCE: 15

```
Met Val Lys Lys Val Ala Ile Ile Gly Ala Gly Ile Ser Gly Leu Ala
1               5                   10                  15

Ser Ile Arg Asn Cys Leu Glu Glu Gly Leu Glu Pro Thr Cys Phe Glu
            20                  25                  30

Lys Gly Glu Asp Ile Gly Gly Leu Trp Lys Phe Ser Asp His Val Glu
        35                  40                  45

Glu Gly Arg Ala Ser Ile Tyr Arg Ser Val Phe Thr Asn Ser Ser Lys
    50                  55                  60

Glu Met Thr Cys Phe Pro Asp Phe Pro Phe Pro Asp Asp Phe Pro Asn
65                  70                  75                  80

Phe Met His Asn Ser Lys Leu Gln Glu Tyr Ile Thr Met Phe Ala Lys
                85                  90                  95

Glu Lys Asn Leu Leu Lys Tyr Ile Gln Phe Lys Thr Ile Val Ser Ser
            100                 105                 110

Val Asn Lys Arg Pro Asp Phe Gln Thr Thr Gly Gln Trp Asp Val Ile
        115                 120                 125

Thr Glu Lys Asp Gly Lys Lys Glu Ser Ala Val Phe Asp Ala Val Met
130                 135                 140

Ile Cys Ser Gly His His Val Tyr Pro Asn Ile Pro Lys Glu Ser Phe
145                 150                 155                 160

Pro Gly Ile Lys Leu Phe Lys Gly Lys Cys Phe His Ser Arg Asp Tyr
                165                 170                 175

Lys Glu Pro Gly Ile Phe Lys Gly Lys Arg Val Leu Val Ile Gly Leu
            180                 185                 190

Gly Asn Ser Gly Cys Asp Ile Ala Ser Glu Leu Ser His Ile Ala Glu
        195                 200                 205

Lys Val Ile Ile Ser Ser Arg Ser Gly Ser Trp Val Met Ser Arg Val
    210                 215                 220

Trp Asp Glu Gly Tyr Pro Trp Asp Met Leu Phe Ile Thr Arg Phe Glu
225                 230                 235                 240

Thr Phe Leu Lys Asn Thr Leu Pro Thr Val Ile Ser Asn Trp Trp Tyr
                245                 250                 255

Met Lys Gln Met Asn Ala Arg Phe Lys His Glu Asn Tyr Gly Leu Met
            260                 265                 270

Pro Leu Asn Ser Thr Leu Arg Lys Glu Pro Val Phe Asn Asp Glu Leu
        275                 280                 285

Pro Ala Cys Ile Leu Cys Gly Ile Val Thr Ile Lys Pro Asn Val Lys
    290                 295                 300

Glu Phe Thr Glu Asp Ser Ala Ile Phe Glu Asp Gly Thr Val Phe Lys
305                 310                 315                 320

Ala Ile Asp Tyr Val Ile Phe Ala Thr Gly Tyr Ser Tyr Ala Tyr Pro
                325                 330                 335

Phe Leu Asp Asp Ser Ile Ile Lys Ser Arg Asp Asn Glu Val Thr Leu
            340                 345                 350
```

-continued

```
Phe Lys Gly Ile Phe Pro Pro Leu Glu Lys Pro Thr Leu Ala Val
        355                 360                 365
Ile Gly Leu Val Gln Ser Leu Gly Ala Ala Ile Pro Thr Thr Asp Leu
    370                 375                 380
Gln Ser Arg Trp Ala Val Gln Val Ile Lys Gly Thr Cys Pro Leu Pro
385                 390                 395                 400
Ser Val Lys Asp Met Met Asn Asp Ile Asp Glu Lys Met Gly Lys Lys
                405                 410                 415
Leu Lys Leu Phe Gly Lys Ser Asp Thr Ile Gln Thr Asp Tyr Val Val
            420                 425                 430
Tyr Met Asp Glu Leu Ala Ser Phe Ile Gly Ala Lys Pro Asn Ile Pro
        435                 440                 445
Trp Leu Phe Leu Thr Asp Pro Lys Leu Ala Leu Glu Val Tyr Phe Gly
    450                 455                 460
Pro Cys Thr Pro Tyr Gln Phe Arg Leu Val Gly Pro Gly Lys Trp Pro
465                 470                 475                 480
Gly Ala Arg Asn Ala Ile Leu Thr Gln Trp Asp Arg Leu Leu Lys Pro
                485                 490                 495
Met Thr Thr Arg Val Val Gly Ser Pro Leu Lys Pro Cys Leu Phe Cys
            500                 505                 510
Asn Trp Phe Arg Pro Val Leu Ile Ser Val Val Ser Ile Ala Ala Leu
        515                 520                 525
Ile Val Leu Phe
    530
```

<210> SEQ ID NO 16
<211> LENGTH: 21
<212> TYPE: DNA
<213> ORGANISM: Artificial Sequence
<220> FEATURE:
<223> OTHER INFORMATION: Primer

<400> SEQUENCE: 16
gatgaaggct atccatggga c                                             21

<210> SEQ ID NO 17
<211> LENGTH: 24
<212> TYPE: DNA
<213> ORGANISM: Artificial Sequence
<220> FEATURE:
<223> OTHER INFORMATION: Primer

<400> SEQUENCE: 17
taaaggcatc aagccgtagt tctc                                          24

<210> SEQ ID NO 18
<211> LENGTH: 18
<212> TYPE: DNA
<213> ORGANISM: Artificial Sequence
<220> FEATURE:
<223> OTHER INFORMATION: Primer

<400> SEQUENCE: 18
tgaggaatgt ttcaaatc                                                 18

<210> SEQ ID NO 19
<211> LENGTH: 27
<212> TYPE: DNA
<213> ORGANISM: Artificial Sequence
<220> FEATURE:

```
<223> OTHER INFORMATION: Primer

<400> SEQUENCE: 19
ggacttagac acacagaaga aaagaag                                           27

<210> SEQ ID NO 20
<211> LENGTH: 29
<212> TYPE: DNA
<213> ORGANISM: Artificial Sequence
<220> FEATURE:
<223> OTHER INFORMATION: Primer

<400> SEQUENCE: 20
gaggtgtgaa attcttattt tttaaatag                                         29
```

DETECTION OF MUTATIONS

CROSS REFERENCE TO RELATED APPLICATIONS

This application is a National Stage application under 35 U.S.C. § 371 that claims the benefit of International Patent Application Serial Number PCT/IB03/00028, filed 9 Jan. 2003, which claims the benefit of Danish Application Number PA 2002 00031, filed 9 Jan. 2002. This application claims priority to International Patent Application Serial Number PCT/IB03/00028 and Danish Application Number PA 2002 00031. In addition, the disclosure of these prior applications are considered part of (and are incorporated by reference in) the disclosure of this application.

FIELD OF INVENTION

The invention relates to mutations in the flavin-containing monooxygenase (FMO3) gene and methods for detection of such mutations in farm animals and poultry.

BACKGROUND OF INVENTION

Occurrence of fishy off-flavor in cow's milk

Fishy off-flavor in milk is a quality defect recently observed in bulk milk in Sweden, which causes considerable losses to both milk producers and dairy companies. Statistical data from an investigation made 1999 regarding the occurrence of off-flavor in milk showed that out of roughly 2,100 herds, 115 (i.e. >5%) had received one or more complaints about fishy off-flavor in bulk milk. Altogether, these 115 herds had received 242 complaints about a moderate fishy off-flavor, whereas 18 bulk milk samples were classified as having a pronounced fishy odor/taste. Exact figures on the current prevalence of fishy odor among Swedish dairy cows are difficult to estimate as no routine organoleptic testing on milk from individual cows is performed. However, when random samples of bulk milk from individual farms were judged to have a fishy off-flavor, tests on samples from individual cows were sometimes performed. These tests have shown that the off-flavor most often originates from one or a few cows within a herd. In order to exceed the threshold above which the test panel perceives a fishy off-flavor in the farm bulk milk, a sufficiently high proportion of the total milk must come from affected cows. Consequently, an individual cow with a fishy off-flavor in the milk will go undetected unless she belongs to a fairly small herd. The above figure of 5% is thus likely an underestimate of the problem. To what extent this off-flavor occurs in other countries is not known, as the vast majority do not perform regular tests for off-flavor in bulk milk at the farm level. There are so far no indications that the defect has any fatal effects on traits subjected to natural selection, like calf survival, or traits included in the breeding goal for milk production.

Characteristics

Fishy off-flavor is characterized by a distinct, unpleasant taste and smell, reminiscent of rotting fish. A fishy smell in milk (Humphriss, 1953; Corfield, 1955) and coffee cream (Eyer et al. 1990) has previously been reported in connection with bacterial degradation of lecithin, choline, and betaine, the latter two being intermediate products in the breakdown of lecithin to trimethylamine (TMA) oxide with TMA as an intermediate compound. A further potential source of fishy taint was related to selective oxidation of butterfat (Swoboda & Peers, 1977). The human nose is extremely sensitive to the TMA odor (Ayesh & Smith, 1990), e.g. the olfactory threshold for detection in milk lies around 1-2 ppm (Metha et al. 1974; von Gunten et al. 1976). As a consequence, milk from a few affected cows in a herd has been shown to be sufficient to cause a fishy off-flavor to the whole bulk milk. There have been a few reports on fishy odor in milk related to TMA content in milk from cows on wheat pasture (Metha et al. 1974; von Gunten et al. 1976; Kim et al. 1980).

Similar Phenomena in Other Species

Problems with fishy odor associated with elevated TMA levels have been described in human ('Fish-odor syndrome' or 'Trimethylaminuria', OMIM #602079, http://www.ncbi.nim.nih.gov) and chicken (Hobson-Frohock et al. 1973). In human, abnormal secretion of TMA has been observed in breath, urine, sweat, saliva, and vaginal secretions (Humbert et al. 1970), whereas in chicken the TMA has predominantly been found in egg yolk (Hobson-Frohock et al. 1973). The TMA is derived from the intestinal degradation of food/feed components rich in TMA or its precursors. Under normal conditions the TMA produced is oxidized to the odor—and tasteless compound TMA-oxide by the liver enzyme flavin-containing monooxygenase (FMO) (Hiavica & Kehl, 1977). The TMA oxide is thereafter excreted in the urine (Al Waiz et al. 1987a). The fishy odor is a consequence of impaired oxidation of TMA (Pearson et al. 1979; Spellacy et al. 1979).

Genetic Causes

The fishy odor shows a recessive mode of inheritance in human (Al-Walz et al. 1987b, 1987c; Ayesh et al. 1993) whereas in chicken it is described as 'semidominant' because the expression has been shown to be dependent on the ingestion of e.g. rapeseed meal (Bolton et al. 1976). In human, parents heterozygous for the defect were shown to excrete elevated amounts of TMA in the urine when given oral doses of 600 mg TMA (Al-Waiz et al. 1987c, 1989; Ayesh et al. 1990, 1993). However, in none of the cases did the treatment result in a fishy odor.

The fishy odor syndrome in humans has recently been shown to be due to mutations in FMO3 encoding an isoform of flavin-containing monooxygenase (Dolphin et al. 1997b; Treacy et al. 1998; Akerman et al. 1999; Basarab et al. 1999; Forrest et al. 2001). The gene has been localized to chromosome 1q23-q25 (http://www.ncbi.nim.nih.gov/LocusLink, August 2001) and its genomic sequence is known (Dolphin et al. 1997a). The human FMO3 gene contains one non-coding and 8 coding exons and is 22.5 kb long. (GenBank AH006707, GenBank AL021026)

Dietary Causes

The elevated concentration of TMA observed in various tissues in human, chicken, and cattle is likely to be due to a combination of genetic and dietary effects. Feed components rich in TMA precursors such as betaine, choline and sinapin, are beet products, green leaves and cereals, and rapeseed products. A high intake of these products may result in an accumulation of TMA, which in turn overloads the enzyme system. Rapeseed also contains progoitrin, a substance that in chicken has been shown to act as an FMO inhibitor by competing with TMA for the enzyme's active binding site (Pearson et al. 1982). In humans, the major source of TMA is marine fish and other seafoods (Zhang et al. 1999).

DESCRIPTION OF THE INVENTION

Figure 1:
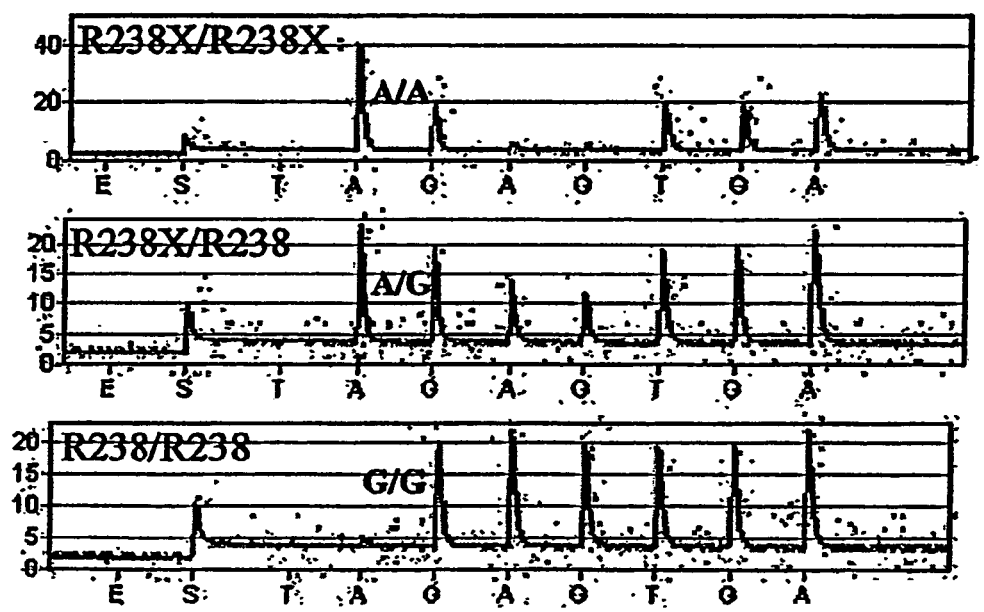
FIG. 1. (a) Alignment of codon 236-238 for the normal (R238) and mutant (R238X) FMO3 allele in cattle. This region was analyzed using pyrosequencing. The location of the sequencing primer and the six positions sequenced are indicated. (b) Pyrosequencing results from the three different genotypes at codon 238. The sequenced reverse strand has the sequence (A/G)AGTGA where the A/G polymorphism corresponds to the R238X nonsense mutation.

According to the invention it is shown that the FMO3 nonsense mutation R238X causes fishy off-flavor in milk. This is the first identified gene that has a profound influence on perceived quality of raw milk. The genotyping method described in this study can now be used by the breeding organisations to eliminate the problem in those breeds where a FMO3 nonsense mutation is present.

The present invention provides a polypeptide which is a flavin-containing monooxygenase 3 (FMO3), wherein said FMO3 is a polypeptide comprising at least a sequence having at least 85% identity, preferably at least 90% identity, more preferably at least 95% identity, with the polypeptide sequence SEQ ID NO: 15.

The present invention further provides polypeptides which are flavin-containing monooxygenase 3 (FMO3), wherein said FMO3 is a polypeptide having at least 85% identity, preferably at least 90% identity, more preferably at least 95% identity, with the polypeptide sequence SEQ ID NO: 15.

An example of such a polypeptide is the bovine FMO3 as shown in SEQ ID NO: 15. Further examples of polypeptides of the invention are the sheep and goat FMO3.

The present invention also provides polypeptides which are functionally altered mutants of flavin-containing monooxygenase 3 (FMO3), wherein said FMO3 is a polypeptide comprising at least a sequence having at least 85% identity, preferably at least 90% identity, more preferably 95% identity, with the polypeptide sequence SEQ ID NO: 15.

In the present context, an animal is considered to refer to all animal species, with the exception of humans.

In a preferred aspect, the present invention is directed towards mutants which result in buildup of TMA resulting in fishy taste and/or smell in an animal. Such mutants includes, but are not limited to, mutants of FMO3 with a decreased catalytic activity towards TMA oxidation.

An example of such a functionally altered mutant is a polypeptide resulting from a deletion of a part of the FMO3 polypeptide, such as the R238X variant of the bovine FMO3.

Other examples of polypeptides which are functionally altered mutants of flavin-containing monooxygenase 3 (FMO3) according to the invention, may arise from insertions, deletions, and mis-sense mutations in the FMO3 gene.

The present invention further provides isolated nucleic acid sequences encoding flavin-containing monooxygenase 3 (FMO3), wherein said FMO3 is a polypeptide comprising at least a sequence having at least 85% identity, preferably at least 90% identity, more preferably at least 95% identity, with the polypeptide sequence SEQ ID NO: 15.

Examples of such isolated nucleic acids are the cDNA sequence encoding the bovine FMO3 shown in SEQ ID NO: 14, the bovine FMO3 gene, or fragments thereof. Examples of such fragments are exons 3, 6, 7 and 9 shown as SEQ ID Nos: 9, 10, 11, and 12, respectively.

Nucleic acid sequences of the invention Include variants of the FMO3 gene, such as the R238X and E287G variants of the bovine FMO3 gene.

To determine the percent identity of two amino acid sequences or of two nucleic acids sequences, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) Proc. Natl. Acad. Sci. USA 87:2264-2268, modified as in Karlin and Altschul (1993) Proc. Natl. Acad. Sci. USA 90:5873. Such an algorithm is incorporated into the NBLAST and XBLAST programs of Altschul, et al. (1990) J. Mol. Biol. 215:403-410. BLAST nucleotide searches can be performed with the NBLAST program, score=100, wordlength=12, to obtain nucleotide sequences homologous to a nucleic acid molecules of the Invention. BLAST protein searches can be performed with the XBLAST program, score=50, wordlength=3 to obtain amino acid sequences homologous to a protein molecule of the invention. To obtain gapped alignments for comparison purposes, Gapped BLAST can be utilized as described in Altschul et al. (1997) Nucleic Acids Res. 25:3389. Alternatively, PSI-Blast can be used to perform an iterated search which detects distant relationships between molecules. When utilizing BLAST, Gapped BLAST, and PSI-Blast programs, the default parameters of the respective programs (e.g., XBLAST and NBLAST) can be used. See http://www.ncbi.nlm.nih.gov.

The percent identity between two sequences can be determined using techniques similar to those described above, with or without allowing gaps. In calculating percent identity, only exact matches are counted.

The invention also includes specific fragments of a nucleic acid sequence of the invention. "Specific fragment" refers to a nucleic acids fragment having a sequence that Is found only in the nucleic acid sequences of the invention, and is not found in nucleic acid sequences encoding related polypeptides such as FMO1, FMO2, FMO4, and FMO5. Such fragments may be, but are not limited to, primers used in amplification reactions such as PCR, or in hybridization experiments. Such fragments are therefore typically at least 10 bp in length, such as at least 15 bp, more preferably at least 20 bp, but may also be longer, such as at least 50 bp or at least 100 bp. The degree of identity between the different FMOs seems to be the same over the whole sequence, the degree of identity between FMO3 and FMO2 (which is the closest relative) being around 60%. The degree of identity between e.g. bovine and human FMO3 is roughly the same over the whole sequence.

"Specifically hybridising fragments" refers to nucleic acid fragments which can hybridize, under stringent conditions only with nucleic acids of the invention, without hybridizing with nucleic acid sequences encoding related polypeptides such as FMO1, FMO2, FMO4, and FMO5.

Said specific fragments or specifically hybridising fragments may for example be used as primers or probes for detecting and/or amplifying nucleic acid sequences encoding FMO3 polypeptides.

Defining appropriate hybridization conditions, including stringent conditions, is within the skill of the art. See, e.g., Molecular Cloning: A Laboratory Manual, 3rd ed., Sambrook et al. eds., Cold Spring Harbor Laboratory Press, 2001; DNA Cloning: A practical Approach, Glover & Hames eds., Oxford University Press, 1996; Nucleic Acid Hybridization: Essential techniques, Ross ed. Wiley, 1998. Thus, stringent hybridization conditions are chosen, by varying the temperature and/or salt concentration in hybridization experiments, such that principally only the molecule of interest hybridizes to the target sequence.

The invention includes sets of primers comprising at least one primer consisting of a specific fragment or specifically hybridising fragment as defined above.

As shown herein, mutations in the bovine FMO3 gene may lead to fish off-flavour of milk, caused by an altered metabolism of trimethylamine.

It is further postulated that mutations in the chicken FMO3 gene may be associated with fish off-flavour of eggs produced by hens carrying such mutations.

The invention also includes a method for detecting a mutation in the FMO3 gene of an animal where the mutation will cause an alteration in the metabolism of trimethylamine leading to a fish off-flavour in a food product of the animal or its offspring, the food product can be any food product collected or produced from animals or their offspring, such as milk or eggs. The animal can be a mammal, excluding humans, used in the production of such food products, such as a cow, a bull, a sheep, or a goat. The animal may also be poultry, such as a hen or a cock.

The method comprises:
obtaining a nucleic acid sample from the animal;
determining the presence in said nucleic acid sample of a nucleic acid sequence encoding a mutated FMO3.

In yet another embodiment the invention provides a method for detecting a nucleic acid sequence comprising a mutation in the FMO3 gene of an animal where the mutation will cause an alteration in the metabolism of trimethylamine leading to a fish off-flavour in a food product of the animal or its offspring.

The method comprises:
obtaining a nucleic acid sample from the animal;
contacting said nucleic acid sample with a nucleic acid probe spanning said mutation under conditions of specific hybridisation between said probe and the mutant sequence to be detected
detecting the hybridisation complex.

Preferably, the process of the invention further comprises, prior to hybridization, PCR amplification from the nucleic acid sample, of a sequence comprising at least the portion of the FMO3 sequence wherein the mutation is to be detected.

Methods allowing the specific hybridisation of a probe only with a perfectly matching complementary sequence, and useful for the detection of punctual mutations are known in the art. They include for instance Allele Specific PCR (Gibbs, Nucleic Acid Res. 17: 2427-2448, 1989), Allele Specific Oligonucleotide Screening (Saiki et al. Nature 324:163-166, 1989).

A mutation in the FMO3 gene may also be detected through detection of polymorphic markers closely linked to said mutation. Such polymorphic markers may be used as surrogate markers for the functional mutation itself, provided that they are in linkage disequilibirum with the mutation. In general, the closer the polymorphic marker is to the mutation itself, the greater the likelyhood that the marker may be used as surrogate marker. However, due to variations in recombination frequencies throughout the genome, the physical distance at which the surrogate marker may be from the mutation is likely to be variable. The invention also provides means for identifying said polymorphic markers, and more specifically polymorphic markers comprised within a genomic DNA sequence comprising at least a portion of a FMO3 gene, and up to 500 kb, preferably 300 kb, more preferably up to 100 kb of a 3' and/or of a 5' adjacent sequence, or the complement thereof. In table 3, examples of polymorphic markers identified In cDNA sequences from normal alleles from a carrier of the R238X mutation and from a homozygous normal individual are provided.

Said polymorphic markers may be obtained for instance, by screening a genomic DNA library from an animal with a probe specific for the FMO3 gene, in order to select clones comprising said nucleic acid sequence and flanking genomic sequences, and identifying a polymorphic marker in said flanking genomic sequences. The allele(s) of a polymorphic marker associated with a given mutant allele of the FMO3 gene may also easily be identified by use of a genomic DNA library from an individual wherein the presence of said mutant allele has previously been detected by hybridisation with a nucleic acid probe of the invention.

Polymorphic markers include for instance, single nucleotide polymorphisms (SNP), microsatellites, insertion/deletion polymorphisms and restriction fragment length polymorphisms (RFLP). These polymorphic markers may be identified by comparison of sequences flanking the FMO3 gene obtained from several individuals. Microsatellites may also be identified by hybridisation with a nucleic acid probe specific of known microsatellite motifs using techniques known to those skilled in the art. Once a polymorphic marker has been identified, a DNA segment spanning the polymorphic locus may be sequenced and a set of primers allowing amplification of said DNA segment may be designed. The invention also encompasses said DNA primers. Design and use of DNA primers for the purpose of amplification by PCR or hybridization is within the skill of the person of ordinary skill. Thus, appropriate primers can be selected from the sequences of the invention using methods known to those skilled in the art.

Detection of a mutation in FMO3 gene may be performed by obtaining a sample of genomic DNA from an animal, amplifying a segment of said DNA spanning a polymorphic marker by PCR using a set of primers of the invention, and detecting In said amplified DNA the presence of an allele of said polymorphic marker associated with said mutation.

The invention also provides kits for the practice of the methods of the invention. A kit comprises at least one specific fragment of a nucleic acid of the invention, or at least one nucleic acid fragment able to hybridise with a nucleic acid sequence of the invention. Said nucleic acid may be labelled using techniques known to those skilled in the art. Examples of suitable labels include, but are not limited to, radioactive labels, fluorescent labels and affinity labels such as biotin. The kits may also comprise a set of primers of the invention. They may be used in conjunction with commercially available amplification kits. They may also include positive and/or negative control reactions or markers, molecular weight size markers for gel electrophoresis, and the like.

A preferred embodiment of the invention relates to the identified R238X mutation In the bovine FMO3 and methods to identify the mutation in order to be able to remove that mutation from stock. The genotyping methods of the present invention can be used to eliminate the problem in those breeds where a FMO3 nonsense mutation, or other mutations leading to fishy odor or taste, is present. A practical way to reduce the problem would be to genotype currently used breeding bulls, bull dams, and young potential breeding bulls before progeny testing, determine which animals are carriers of the mutation(s), and eliminate carriers from breeding. That way, the detrimental mutation(s) can be eliminated from the selected breed.

Realization of the invention can be illustrated by the following examples. These examples should however only be understood as examples of specific embodiments of the present invention, and in no way limiting for its adaptation for other use.

EXAMPLES

Example 1

Sequencing of the Bovine FMO3 Gene

Cattle Samples and DNA Preparation

The present study included two different groups of dairy cattle. The first material comprised 21 cows of the Swedish Red and White breed (SRB) with information from sensory analyses on the milk. Ten of the cows belong to either of the two experimental herds, Jälla and Kungsängen, at Swedish University of Agricultural Sciences in Uppsala. The remaining cows belong to either of four commercial herds, all of which had received complaints about fishy off-flavor in the bulk milk. In three of the six herds, 'control' cows were chosen that were comparable to the affected cows as regards breed, lactation number, and stage of lactation but were producing milk with a normal taste and smell.

A population study was performed in which bulls and cows from the four dairy breeds in Sweden were genotyped for the observed FMO3 nonsense mutation. From each of the two major breeds, SRB and Swedish Holstein, 100 individuals were chosen, whereas from the two small breeds, Swedish Polled and Swedish Jersey, 25 and 23 individuals were sampled, respectively. Genomic DNA was prepared from blood samples according to standard protocols.

PCR amplification and sequencing of the bovine FMO3 gene from genomic DNA samples Exonic parts of the FMO3 gene were amplified from genomic DNA samples using primers corresponding to sequences well conserved between the human, rabbit, mouse, and rat FMO3 sequences available in GenBank (Table 1). Two genomic DNA samples were used, one from a cow that had been shown to repeatedly produce milk with a fishy flavor and the other from a control cow producing normal milk.

Table 1. Primer sequences used for PCR amplification of the bovine FMO3 gene from genomic DNA.

| FMO3 region amplified[1] | Forward (F) and reverse (R) primer sequences 5'-3' | |
|---|---|---|
| exon 3 | F: GACCATGCAGAAGAGGGCAG | SEQ ID NO: 1 |
| | R: CTTAAACTGTATGTATTTCAGGAGGTT | SEQ ID NO: 2 |
| exon 6 | F: CATCATCAGCTCCAGAAGTGG | SEQ ID NO: 3 |
| | R: TAAAGGCATCAAGCCATAGTT | SEQ ID NO: 4 |
| exon 7 | F: CAGAATCCTGAGGAAAGAGCC | SEQ ID NO: 5 |
| | R: ATTACTTGTGCTGCCCAGCG | SEQ ID NO: 6 |
| exon 8-9 | F: GATGAATGATATTAATGAGAAAATGG | SEQ ID NO: 7 |
| | R: CCGGTCCCACTGGGTCAG | SEQ ID NO: 8 |

[1]The numbering of exons is based on the described exon-intron organization for the human FMO3 gene (Dolphin et al. 1997a).

The PCR was performed in 10 µl reactions including 1×PCR buffer, 1.5 mM MgCl$_2$, 0.2 mM of each dNTP, 2.5 pmol of each primer, 25 ng genomic DNA, and 0.35 U AmpliTaq DNA polymerase (Perkin Elmer, Branchburg, N.J., USA). Thermocycling was carried out in a PTC200 machine (MJ Research, Watertown, Mass., USA) and included 40 cycles with annealing at 53° C. for 30 s and extension at 72° C. for 2 min. The denaturation step was 95° C. for 1-2 min in the first two cycles, and 94° C. for 30 s In the remaining cycles. The products were analyzed by agarose gel electrophoresis (4% Nusieve/Seakem 3:1, FMC Bioproducts, Rockland, Me., USA). The PCR products were directly sequenced with BigDye terminators and an ABI377 instrument (Perkin-Elmer, Foster City, Calif., USA). Sequence analysis and comparison of sequences from the cows with fishy flavored and normal milk, respectively, was performed using the Sequencher software (GENE CODES, Ann Arbor, Mich., USA).

Bovine FMO3 Gene Sequences

Bovine FMO3 sequences corresponding to human FMO3 exons 3, 6, 7, 9, and intron 8 were generated and are given in SEQ ID Nos: 9-13. Subsequently, the complete coding region of the bovine FMO3 gene was sequenced from RT-PCR products from liver mRNA. The bovine FMO3 cDNA sequence is given in SEQ ID NO: 14 and the corresponding polypeptide sequence of bovine FMO3 is given in SEQ ID NO: 15. The exonic sequences generated from genomic DNA showed 100% identity to the cDNA sequence obtained from the RT-PCR products and FMO3 specificity was strongly supported by the high sequence similarity to other mammalian FMO3 sequences. For example, a Blast comparison between the complete coding cattle FMO3 sequence obtained here and the corresponding human sequence (GenBank NM_006894) showed 85% and 82% identity at the nucleotide and amino acid levels, respectively.

Identification of a Nonsense Mutation in the Bovine FMO3 Gene

Partial cattle FMO3 sequences obtained from a cow producing milk with strong fishy off-flavor and a cow producing normal milk were compared. The compared sequences included altogether 1522 bp and 808 bp of these represent coding sequence. The coding part includes 268 codons, corresponding to approximately 50% of the protein. The only sequence difference found between the two cows was a C/T nucleotide substitution located at position 62 in exon 6 (SEQ ID NO: 10). The C→T substitution changes the codon for arginine (R) at position 238 to a stop codon (X); the numbering of amino acid positions are based on the human amino acid sequence given in Genbank NM_006894. This nonsense mutation is thus denoted R238X. The pyrosequencing test confirmed that the affected cow was homozygous for the R238X substitution whereas the control cow was homozygous R/R at residue 238 (FIG. 1).

Example 2

Association Between Mutations in FMO3 and the Presence of Fishy of-Flavour in Cow's Milk Genotyping of the FMO3 R238X Nonsense Mutation The identified single nucleotide polymorphism (SNP) in exon 6 was genotyped by pyrosequencing (Ronaghi et al. 1998) using a Luc96 instrument (Pyrosequencing AB, Uppsala, Sweden). This included PCR amplification of a 147 bp product from genomic DNA samples using the forward primer 5'-biotin-GAT GAA GGC TAT CCA TGG GAC (SEQ ID NO: 16) and the reverse primer 5'-TAA AGG CAT CAA GCC GTA GTT CTC (SEQ ID NO: 17). The PCR was performed in 20 µl reactions with concentrations of reagents as above. Thermocycling was carried out in a PE9600 instrument (Perkin-Elmer, Foster City, Calif., USA) and included an initial denaturation step at 94° C. for 2 min followed by 5 cycles with 94° C. for 30 s, 55° C. for 30 s, 72° C. for 45 s, 43 cycles with 94 ° C. for 20 s, 50° C. for 30 s, 72° C. for 45 s, and a final extension step at 72° C. for 5 min. Pyrosequencing on the forward strand was done using the reverse sequencing primer 5' TGA GGA ATG TTT CAA ATC (SEQ ID NO: 18) and conditions according to the manufacturer's recommendations.

RT-PCR Amplification and Sequencing of the Bovine FMO3 cDNA

Ten livers from SRB cattle were collected and the pyrosequencing test showed that two were heterozygous carriers of the R238X mutation. One of these livers as well as one liver from a homozygous wild-type cow were used for mRNA preparation, reverse transcription (RT)-PCR amplification and direct sequencing of the coding FMO3 region. Two additional primers were used for this purpose, designed from sequences in the untranslated regions which showed conservation between other mammalian FMO3 sequences. Thus, the 5'UTR primer 5' GGA CTT AGA CAC ACA GM GAA MG AAG (SEQ ID NO: 19) and the 3'UTR primer 5' GAG GTG TGA AAT TCT TAT TTT TTA AAT AG (SEQ ID NO: 20) were used in pairs with the reverse and forward pyrosequencing PCR primers, respectively. Thus, the coding sequence was amplified in two overlapping pieces, each including the site of the R238X mutation. Poly A mRNA was isolated from cattle livers using the Quickprep mRNA Micro purification kit (Amersham Pharmacia Biotech, Uppsala, Sweden) and RT-PCR was carried out using the First strand cDNA synthesis kit (Amersham Pharmacia Biotech) with ~200 ng mRNA primed with 0.1 µg random hexamers in a 15 µl reaction volume. Two µl of the completed first strand reaction was used in each PCR reaction with a total volume of 12 µl so that the final concentrations of dNTP, $Mg^{2+}$, primers, and AmpliTaq polymerase were the same as above. The thermocycling conditions were as described above for the sequenced genomic DNA amplicons but the 5' part of the cDNA required a repeated PCR to yield enough product for sequencing.

The R238X substitution is closely associated with the presence of fishy off-flavor in cow's milk The pyrosequencing test was used to test a case-control material comprising animals producing milk classified as having a fishy off-flavor and control animals from the same herds (Table 2). A Class 2 score means that two trained persons both classified the sample as having a strong fishy off-flavor whereas Class 1 implies that the two persons judged the fishy off-flavor as strong/moderate, moderate/ moderate or moderate/normal. The results revealed a very strong association between the FMO3 R238X nonsense mutation and strong fishy-off flavor since eight out of nine animals with the Class 2 score were homozygous for this mutation and the ninth was heterozygous. In contrast, the five control samples were homozygous normal. The Class 1 group contained animals of all three genotype classes.

TABLE 2

FMO3 genotype distributions in a group of 21 Swedish Red and White cows with or without fishy off-flavor in milk and in animals representing the four different dairy breeds in Sweden

| | FMO3 genotype at codon 238 | | | |
|---|---|---|---|---|
| | R/R | R/X | X/X | Total |
| Case/control study Sensory evaluation:[1] | | | | |
| Normal | 5 | 0 | 0 | 5 |
| Class 1 | 3 | 3 | 1 | 7 |
| Class 2 | 0 | 1 | 8 | 9 |
| Population study Breed: | | | | |
| Swedish Red and White | 71 | 27 | 2 | 100 |
| Swedish Holstein | 100 | 0 | 0 | 100 |
| Swedish Polled | 25 | 0 | 0 | 25 |
| Swedish Jersey | 23 | 0 | 0 | 23 |

[1]Evaluation based on two trained persons.
Class 2 = both person recognized a strong off-flavor (strong/strong);
Class 1 = strong/moderate, moderate/moderate, moderate/normal.

The R238X Substitution Occurs at a Surprisingly High Frequency in the Swedish Red and White Breed The population screening involved 248 animals representing the four dairy breeds in Sweden. The R238X substitution was not found in Swedish Holstein, Swedish Polled, or Swedish Jersey but was surprisingly common in the Swedish Red and White breed (Table 2). Two homozygous mutant and 27 heterozygotes were observed among 100 animals and the allele frequency estimate for the mutation was as high as 15.5%.

SNPs observed by cDNA sequencing of a heterozygous R238X carrier and a homozygous normal animal Only the wild type transcript appeared well represented In the mRNA sample from the R238X carrier. Only a very weak sequencing signal could be observed from the mutant transcript, at least 10 times weaker than from the wild type transcript. A similar result was obtained using liver mRNA from a second heterozygous R238X carrier. Consequently, we could not search for possible additional mutations present in the FMO3 allele associated with fishy-off flavour. However, the RT-PCR experiment confirmed that the R238X mutation occurs in an expressed FMO3 gene.

The comparison of the full-length liver cDNA sequence from the normal allele from the carrier and from the homozygous normal individual revealed three additional single nucleotide polymorphisms (SNPs), all compiled in Table 3. Only one of the SNPs altered the amino acid sequence, E287G.

TABLE 3

Single nucleotide polymorphisms in the bovine FMO3 gene

| Nucleotide/Amino acid position[1] | Nucleotide/Amino acid change |
|---|---|
| 877/287 | A↔G/E↔G |
| 1067/350 | T↔C/no change |
| 1085/356 | A↔C/no change |

[1]Position as numbered in SEQ ID NO: 14.

Discussion

The present study has provided compelling evidence for that the observed FMO3 nonsense mutation R238X causes fishy off-flavor in milk. This conclusion is based on (i) the identification of an obvious loss-of-function mutation in a gene associated with a similar syndrome in humans, (ii) a very strong association between the presence of this mutation and a strong fishy-off flavor in a case/control material and finally (iii) the presence of this mutation in the only breed (SRB) tested with well documented cases of a fishy off-flavor.

The R238X mutation causes a premature termination eliminating more than 50% of the FMO3 enzyme which is expected to comprise 532 amino acids as in the human FMO3 protein. Similar nonsense mutations in humans (E305X, E314X) have been shown to lead to a complete loss of enzyme activity (Treacy et al. 1998, Akerman et al. 1999). Moreover, we observed only barely detectable levels of the mutant transcript in liver mRNA from two heterozygous carriers of R238X. This is most probably explained by nonsense-mediated mRNA decay (NMD; Culbertson 1999). It is very likely that cows homozygous for the R238X mutation show a complete lack of FMO3 activity necessary for the oxidation of TMA to an odorless compound. This provides a plausible explanation for the fishy off-flavor of the milk from these cows. Milk samples from five of the cows homozygous for the mutation and included in this study have previously been analyzed for TMA content using dynamic headspace gas chromatography. The results showed that these milk samples all had comparatively high concentrations of TMA whereas the milk from normal cows showed non-detectable or, in a few cases, very low TMA concentrations.

The results suggested a recessive mode of inheritance for the fishy-off flavor in cows milk in agreement with the recessive inheritance of the fishy-odor syndrome in humans. However, there was not a perfect agreement between this model and the observations from the case/control study since one carrier was scored as having strong fishy off-flavor (Class 2) and one homozygous mutant showed a moderate off-flavor (Class 1). We think there are two potential explanations from this deviation from a strict recessive model. The fishy-off flavor is influenced by environmental factors, like the presence of TMA precursors or FMO inhibitors in the feed. For example, the TMA concentration in the milk from one of the homozygous mutants was shown to vary between 1 and 16 mg TMA/kg milk within a single lactation. Secondly, the sensory evaluation is a somewhat subjective measure. The test panel consisting of two trained persons goes through a considerable number of milk samples during one day and may have some difficulties to discern the various off-flavors present in the milk samples and also to discriminate between different flavors.

In the present material the mutation was only observed among the SRB animals, but at a relatively high frequency. This is in complete accordance with the experiences made by the staff at the milk analysis laboratory that performed the sensory analysis, who have so far only encountered the fishy off-flavor in milk from SRB cows. We analyzed the pedigree data for all carriers and homozygous mutants but we did not find any common ancestor of these animals within the last 10 generations. The results suggest that the mutation has been present in the existing SRB population for a relatively long period of time. The origin of the mutation probably dates back at least to the beginning of the last century, judging from the available pedigree information on affected animals. Moreover, the pedigree data Indicate that the mutation may exist in other cattle populations closely related to the Ayrshire.

To the best of our knowledge, this is the first identified gene that has a profound influence on perceived quality of raw milk. The genotyping method described in this study can now be used by the breeding organisations to eliminate the problem in those breeds where a FMO3 nonsense mutation is present. A practical way to reduce the problem would be to genotype currently used breeding bulls, bull dams, and young potential breeding bulls before progeny testing and eliminate carriers from breeding.

Example 3

Sequencing of the Chicken FMO3 Gene

Exonic parts of the chicken FMO3 gene will be amplified from genomic DNA samples using both primers corresponding to sequences well conserved between the bovine, human, rabbit, mouse, and rat FMO3 sequences as well as primers corresponding to EST sequences derived from the chicken FMO3 gene, ESTs 603149708F1 and 603610105 µl available in the Chicken EST database (http://www.chick.umist.ac.uk/cgi-bin/chicken_database.cgi). Both genomic DNA samples from hens that have been shown to produce eggs with a fishy off-flavor and genomic DNA samples from normal hens will be used as templates. The sequence of cDNA coding for the chicken FMO3 will be obtained from RT-PCR products from liver mRNA.

The sequences obtained from hens that have been shown to produce eggs with a fishy off-flavor and sequences obtained from normal hens will be compared and sequence variants identified.

Hens will be genotyped and FMO3 variants associated with production of eggs with fishy off-flavour will be identified.

REFERENCES

Akerman, B. R., Forrest, S., Chow, L., Youil, R., Knight, M. & Treacy, E. P. 1999. Two novel mutations of the FMO3 gene in a proband with trimethylaminuria. *Human Mutation* 13:376-379

Al-Waiz, M., Mitchell, S. C., Idle, J. R. & Smith, R. L. 1987a. The metabolism of $^{14}$C-labelled trimethylamine and its N-oxide in man. *Xenobiotica* 17:551-558

Al-Waiz, M., Ayesh, R., Mitchell, S. C., Idle, J. R. & Smith, R. L. 1987 b. Trimethylaminuria (fish-odour syndrome)—An inborn error of oxidative metabolism. *The Lancet* 8533:634-635

Al-Waiz, M., Ayesh, R., Mitchell, S. C., Idle, J. R. & Smith, R. L. 1987c A genetic polymorphism of the N-oxidation of trimethylamine in humans. *Clinical Pharmacology and Therapeutics* 42:588-594

Al-Waiz, M., Ayesh, R., Mitchell, S. C., Idle, J. R. & Smith, R. L. 1989. Trimethylaminuria: the detection of carriers using a trimethylamine load test. *Journal of Inherited Metabolic Disease* 12:80-85

Ayesh, R. & Smith, R. L. 1990. Genetic polymorphism of trimethylamine oxidation. *Pharmacology & Therapeutics* 45:387-401

Ayesh, R., Mitchell, S. C., Zhang, A. & Smith, R. L. 1993. The fish odour syndrome: biological, familial, and clinical aspects. *British Medical Journal* 307: 655-657

Basarab, T. B., Ashton, G. H. S., Menage, H. duP. & McGrath, J. A. 1999. Sequence variation in the flavin-containing mono-oxygenase 3 gene (FMO3) in fish odour syndrome. *British Journal of Dermatology* 140: 164-167

Bolton, W., Carter, T. C. & Morley Jones, R. 1976. The hen's egg: Genetics of taints in eggs from hens fed on rapeseed meal. *British Poultry Science* 17: 313-320

Corfield, A. 1955. Bacterial fishiness in milk. *Dairy Industries* December: 1035-1037

Culbertson, M. R. 1999 RNA surveillance unforeseen consequences for gene expression, inherited genetic disorders and cancer. *Trends in Genetics* 15:74-80

Dolphin, C. T., Riley, J. H., Smith, R. L., Shepard, E. A. & Phillips, I. R. 1997 a. Structural organization of the human flavin-containing monooxygenase 3 gene (FMO3), the favoured candidate for fish-odor syndrome, determined directly from genomic DNA. *Genomics* 46: 260-267

Dolphin, C. T., Janmohamed, A., Smith, R. L., Shepard, E. A. & Phillips, I. R. 1997b. Missense mutation in flavin-containing mono-oxygenase 3 gene, FMO3, underlies fish-odour syndrome. *Nature genetics* 17: 491-494

Eyer, H., Gauch, R. & Bosset, J. O. 1990. Untersuchung des Fehlaromas "fischig" in Kaffeerahm [The fishy off-flavour of coffee cream]. *Schweizerische Milchwirtschaftliche Forschung* 19:43-45

Forrest, S. M., Knight, M., Akerman, B. R., Cashman, J. R. & Treacy, E. P. 2001. A novel deletion in the flavin-containing monooxygenase gene (FMO3) in a Greek patient with trimethylaminuria. *Pharmacogenetics* 11: 169-174

Hlavica, P. & Kehl, M. 1977. Studies on the mechanism of hepatic microsomal N-oxide formation, the role of cytochrome P-450 and mixed function amine oxidase in the N-oxidation of N,N-dimethylamine. *Biochemical Journal* 164: 487-496

Hobson-Frohock, A., Land, D. G., Griffiths, N. M. & Curtis, R. F. 1973. Egg taints: association with trimethylamine. *Nature* 243: 304-305

Humbert, J. R., Hammond, K. B., Hathaway, W. E., Marcoux, J. G. & O'Brien, D. 1970. Trimethylaminuria: the fish-odour syndrome. *The Lancet* 2: 770-771 Humphriss, E. 1953. Chromogenic bacteria and milk. Dairy Industries September :781-782

Kim, H. S., Gilliland, S. E., & Von Gunten, R. L. 1980. Chemical test for detecting wheat pasture flavor in cow's milk. *Journal of Dairy Science* 63:368-374

Metha, R. S., Bassette, R. & Ward, G. 1974. Trimethylamine responsible for fishy flavor in milk from cows on wheat pasture. *Journal of Dairy Science* 57:285-289

Pearson, A. W., Butler, E. J., Curtis, R. F., Fenwick, G. R., Hobson-Frohock, A. & Land, D. G. 1979. Effect of rapeseed meal on trimethylamine metabolism in the domestic fowl in relation to egg taint. *Journal of the Science of Food and Agriculture* 30:799-804

Pearson, A. W., Greenwood, N. M., Butler, E. J. & Fenwick, G. R. 1982. The effects of thionamides and related compounds on trimethylamine oxidase activity in hepatic microsomes isolated from chickens (*Gallus domesticus*). *Comparative Biochemistry and Physiology. C: Comparative Pharmacology* 73C: 389-393

Ronaghi, M., Uhlén, M. & Nyrén, P. 1998. A sequencing method based on real-time pyrophosphate. *Science* 281: 363, 365.

Spellacy, E., Watts, R W. E. & Gollamali, S. K. 1979. Trimethylaminuria. *Journal of Inherited Metabolic Disease* 2: 85-88

Swoboda, P. A. T., & Peers, K. E. 1977. Volatile odorous compounds responsible for metallic, fishy taint formed in butterfat by selective oxidation. *Journal of the Science of Food and Agriculture* 28: 1010-1018

Treacy, E. P., Akerman, B. R., Chow, L. M. L., Youil, R., Bibeau, C., Lin, J., Bruce, A. G., Knight, M., Danks, D. M., Cashman, J. R. & Forrest, S. M. 1998. Mutations of the flavin-containing monooxygenase gene (FMO3) cause trimethylaminuria, a defect in detoxication. *Human Molecular Genetics* 7: 839-845

Von Gunten, R. L., Bush, L. J., Odell, G. V., Wells, M. E. & Adams, G. D. 1976. Factors related to the occurrence of trimethylamine in milk. *Journal of Milk and Food Technology* 39 526-529

Zhang, A. Q., Mitchell, S. C. & Smith, R. L. 1999. Dietary precursors of trimethylamine in man: a pilot study. *Food and Chemical Toxicology* 37: 515-520

---

The invention claimed is:

1. A method for detecting a nucleic acid sequence comprising a mutation in the FMO3 gene of a bovine animal, where the mutation will cause an alteration in the metabolism of trimethylamine leading to a fish off-flavour in a food product of the animal or its offspring, wherein the method comprises:
   (a) obtaining a nucleic acid sample from the animal; and
   (b) determining the presence in said nucleic acid sample of a nucleic acid sequence encoding a mutated FMO3 polypeptide, wherein the mutation is a R238X mutation of the polypeptide sequence SEQ ID NO:15.

2. A method for detecting a nucleic acid sequence according to claim 1, wherein said nucleic acid sequence is detected by
   (a) contacting said nucleic acid sample with a nucleic acid probe spanning said mutation under conditions of specific hybridisation between said probe and the mutant sequence to be detected; and
   (b) detecting the hybridisation complex.

3. A method according to claim 1 wherein the presence of the nucleic acid sequence encoding said mutant polypeptide is determined by contacting the nucleic acid sample with a nucleic acid fragment selected from the group consisting of:
   (i) a specific fragment of a nucleic acid sequence encoding a polypeptide which is a flavin-containing monooxygenase 3 (FMO3), wherein said FMO3 is the polypeptide sequence SEQ ID NO:15 and
   (ii) SEQ ID NO:9,
   (iii) SEQ ID NO:10,
   (iv) SEQ ID NO:11,
   (v) SEQ ID NO:12,
   (vi) SEQ ID NO:16,
   (vii) SEQ ID NO:17, and
   (viii) SEQ ID NO:18.

4. A method according to claim 1 which further comprises PCR amplification from the nucleic acid sample, of a sequence comprising at least the portion of the FMO3 sequence wherein the mutation is to be detected.

5. A method according to claim 1, wherein the presence of the nucleic acid sequence encoding said mutant polypeptide is determined by contacting the nucleic acid sample with a nucleic acid fragment which specifically hybridises with a nucleic acid sequence encoding a polypeptide which is a flavin-containing monooxygenase 3 (FMO3), wherein said FMO3 is the polypeptide sequence SEQ ID NO:15.

6. A method according to claim 1, wherein the presence of the nucleic acid sequence encoding said mutant polypeptide is determined by contacting the nucleic acid sample with a nucleic acid fragment which specifically hybridises with (i) a nucleic acid sequence comprising at least a portion of a nucleic acid sequence encoding a polypeptide which is a flavin-containing monooxygenase 3 (FMO3), wherein said FMO3 is the polypeptide sequence SEQ ID NO:15, and up to 500 kb of a 3' and/or a 5' adjacent genomic DNA sequence, or (ii) the complement thereof.

7. A method according to claim 1, wherein the nucleic acid sample is a sample of genomic DNA from the animal.

* * * * *

UNITED STATES PATENT AND TRADEMARK OFFICE
CERTIFICATE OF CORRECTION

PATENT NO. : 7,273,703 B2  Page 1 of 1
APPLICATION NO. : 10/501032
DATED : September 25, 2007
INVENTOR(S) : Anne Lunden, Leif Andersson and Stefan Marklund It is certified that error appears in the above-identified patent and that said Letters Patent is hereby corrected as shown below:

Column 29, line 48 through Column 30, line 24, please delete

"(ii) SEQ ID NO:9,
(iii) SEQ ID NO:10,
(iv) SEQ ID NO:11,
(v) SEQ ID NO:12,
(vi) SEQ ID NO:16,
(vii) SEQ ID NO:17, and
(viii) SEQ ID NO:18"

and insert --(ii) SEQ ID NO:10-- therefor.

Signed and Sealed this

Twenty-fifth Day of November, 2008

JON W. DUDAS
*Director of the United States Patent and Trademark Office*